United States Patent
Jung

(10) Patent No.: US 9,668,837 B2
(45) Date of Patent: Jun. 6, 2017

(54) CREATING A TRANSLUCENT EFFECT WITHIN ONE HALF OF A GREEN BODY ZIRCONIA BLANK

(71) Applicant: Benjamin Y. Jung, West Valley City, UT (US)

(72) Inventor: Benjamin Y. Jung, West Valley City, UT (US)

(73) Assignee: B & D Dental Corporation, West Valley City, UT (US)

( * ) Notice: Subject to any disclaimer, the term of this patent is extended or adjusted under 35 U.S.C. 154(b) by 0 days.

(21) Appl. No.: 15/099,914

(22) Filed: Apr. 15, 2016

(65) Prior Publication Data

US 2016/0228223 A1 Aug. 11, 2016

Related U.S. Application Data

(63) Continuation-in-part of application No. 14/559,571, filed on Dec. 3, 2014, which is a continuation of (Continued)

(51) Int. Cl.
*A61C 13/00* (2006.01)
*A61C 13/08* (2006.01)
(Continued)

(52) U.S. Cl.
CPC ...... *A61C 13/0022* (2013.01); *A61C 13/0004* (2013.01); *A61C 13/0006* (2013.01); (Continued)

(58) Field of Classification Search
None
See application file for complete search history.

(56) References Cited

U.S. PATENT DOCUMENTS 5,482,732 A * 1/1996 Kramer ............... A61C 13/082
433/203.1
6,354,836 B1 3/2002 Panzera et al.
(Continued)

FOREIGN PATENT DOCUMENTS

WO WO2011/156602 12/2011
WO WO2013/003990 1/2013
WO WO2014/062375 4/2014

OTHER PUBLICATIONS

Hongbo Guo et al.; Laminated and functionally graded hydroxyaptite/yttria stabilized tetragonal zirconia composites fabricated by spark plasma sintering; Biomaterials; 2003; pp. 667-675; vol. 24; Elsevier Science Ltd.

(Continued)

*Primary Examiner* — David Sample
*Assistant Examiner* — Nicholas W Jordan
(74) *Attorney, Agent, or Firm* — Thorpe, North & Western, LLP

(57) ABSTRACT

A dental block for producing a dental prosthesis comprises a green body including zirconia and having a chemical composition including increasing amounts of a chroma component, such as manganese, through a thickness of the green body. The green body is substantially white with a substantially consistent optical characteristic of chroma across the thickness, and is subsequently millable and sinterable to form the dental prosthesis with an optical characteristic of decreasing gray color through a thickness of the dental prosthesis.

13 Claims, 3 Drawing Sheets

Related U.S. Application Data application No. 13/403,417, filed on Feb. 23, 2012, now Pat. No. 8,936,848.

(60) Provisional application No. 62/147,992, filed on Apr. 15, 2015.

(51) Int. Cl.
*A61K 6/02* (2006.01)
*B32B 18/00* (2006.01)
*C04B 35/486* (2006.01)

(52) U.S. Cl.
CPC ............ *A61C 13/082* (2013.01); *A61K 6/021* (2013.01); *A61K 6/024* (2013.01); *B32B 18/00* (2013.01); *C04B 35/486* (2013.01); *C04B 2235/3225* (2013.01); *C04B 2235/3246* (2013.01); *C04B 2235/5445* (2013.01); *C04B 2235/608* (2013.01); *C04B 2235/612* (2013.01); *C04B 2235/6567* (2013.01); *C04B 2235/77* (2013.01); *C04B 2235/96* (2013.01); *C04B 2235/9615* (2013.01); *C04B 2235/9653* (2013.01); *C04B 2235/9661* (2013.01); *C04B 2237/348* (2013.01); *C04B 2237/582* (2013.01); *C04B 2237/704* (2013.01); *Y10T 428/24934* (2015.01); *Y10T 428/24967* (2015.01)

(56) References Cited

U.S. PATENT DOCUMENTS

| | | | |
|---|---|---|---|
| 7,011,522 | B2 | 3/2006 | Panzera et al. |
| 7,090,721 | B2 | 8/2006 | Craug et al. |
| 7,691,497 | B1 | 4/2010 | Brodkin et al. |
| 7,981,531 | B2 | 7/2011 | Rheinberger et al. |
| 8,025,992 | B2 | 9/2011 | Engels et al. |
| 8,936,848 | B2 | 1/2015 | Jung et al. |
| 9,212,065 | B2* | 12/2015 | Yamada ............ A61C 13/0022 |
| 2004/0232576 | A1 | 11/2004 | Brodkin et al. |
| 2007/0292597 | A1 | 12/2007 | Ritzberger et al. |
| 2008/0064011 | A1 | 3/2008 | Rheinberger et al. |
| 2008/0274440 | A1 | 11/2008 | Smith et al. |
| 2008/0303181 | A1 | 12/2008 | Holand et al. |
| 2009/0092531 | A1 | 4/2009 | Katusic et al. |
| 2010/0133711 | A1 | 6/2010 | Brodkin et al. |
| 2010/0209876 | A1 | 8/2010 | Wagner et al. |
| 2010/0216095 | A1 | 8/2010 | Scharf |
| 2011/0236855 | A1 | 9/2011 | Rheinberger et al. |
| 2011/0236860 | A1 | 9/2011 | Jahns et al. |
| 2011/0319254 | A1 | 12/2011 | Rheinberger et al. |
| 2012/0139141 | A1 | 6/2012 | Kahan et al. |
| 2013/0115365 | A1 | 5/2013 | Wang et al. |
| 2013/0221554 | A1 | 8/2013 | Jung et al. |
| 2013/0231239 | A1 | 9/2013 | Carden et al. |
| 2014/0370464 | A1* | 12/2014 | Kounga ............ A61C 13/0022 433/212.1 |
| 2015/0173869 | A1 | 6/2015 | Jung et al. |

OTHER PUBLICATIONS

U.S. Appl. No. 13/403,494, filed Feb. 23, 2012; Yunoh Jung; office action dated Mar. 14, 2014.

Akira Hasegawa, "Color and Translucency of In Vivo Natural Central Incisors"; Apr. 2000, the journal of Prosthetic Dentistry, vol. 83; pp. 418-422.

John M. Powers, "Guide to All Ceramic Bonding"; Jun. 5, 2012; Kurarydental.com, pp. 1-12.

U.S. Appl. No. 13/403,494, filed Feb. 23, 2012; Yunoh Jung; office action dated Jun. 6, 2013.

\* cited by examiner

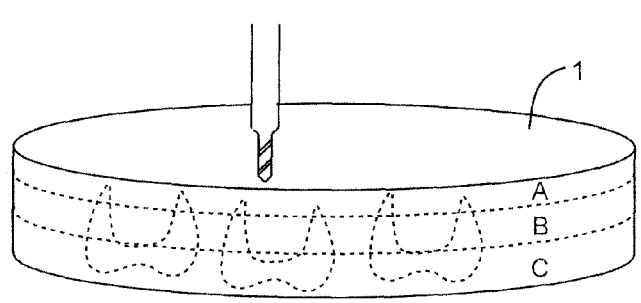
Fig 1a
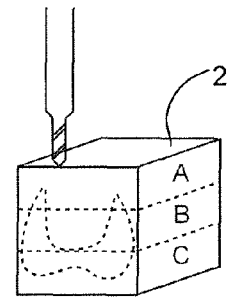
Fig 1b
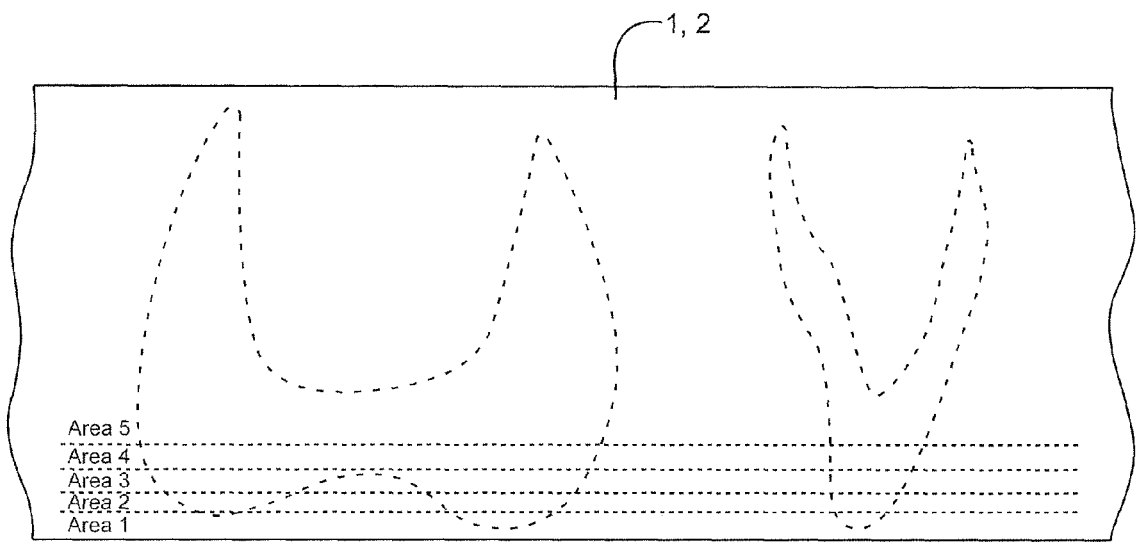
Fig 2a
Fig 2b
| Area | Amount of manganese (wt %) |
|---|---|
| Area 1 | Z |
| Area 2 | Y |
| Area 3 | X |
wherein, $X < Y < Z$

CREATING A TRANSLUCENT EFFECT WITHIN ONE HALF OF A GREEN BODY ZIRCONIA BLANK

PRIORITY CLAIM

This is a continuation-in-part of U.S. Provisional patent application Ser. No. 14/559,571, filed on Dec. 3, 2014; which is a continuation of U.S. patent application Ser. No. 13/403,417, filed Feb. 23, 2012, now U.S. Pat. No. 8,936,848; which are hereby incorporated herein by reference in their entirety.

Priority is claimed to copending U.S. Provisional Patent Application Ser. No. 62/147,992, filed Apr. 15, 2015, which is hereby incorporated herein by reference in its entirety.

BACKGROUND

Field of the Invention

The present invention relates generally to a dental block for producing a dental prosthesis. More particularly, the present invention relates to a dental blank to create a more translucent effect within one portion of a green body zirconia blank, and a method of making.

Related Art

Typically, a natural human tooth has a more translucent structure at its outer or cervical portion. U.S. Pat. No. 8,025,992 (Engels) introduces a milling blank with two components each existing from one side to the other in an inverse way. In a human tooth, however, the translucent effect exists, at most, only in the top one third of the tooth. US Publication 2004/0232576 (Pentron) introduces use of manganate as a pigment for porcelain composition.

SUMMARY OF THE INVENTION

It has been recognized that it would be advantageous to develop a dental blank with an area that is more translucent in its structure than another area to mimic the natural aspect of a human tooth. In order to have this aspect, one portion or half of the blank can have more chroma component and another portion or half can have a more translucent aspect. In one aspect, the translucent aspect can be limited to one third of the blank, and up to half of the blank. The invention provides a dental blank wherein the green body has a first chroma component mainly in one portion of half of the blank, and a second chroma component mainly in another portion or half of the blank, with the second chroma component not extending into the portion or half with the first chroma component. By adding more manganese content, for example, as a second chroma component, the zirconia green body, after being finally sintered, takes on a slightly graying effect in one portion or half of the blank, thereby creating a tooth image that is more natural like a human tooth.

The invention provides a dental block for producing a dental prosthesis. The dental block comprises a green body comprising zirconia. The green body has multiple different layers, each having a different chemical composition between adjacent layers. The green body has a first chroma component mainly in one half of the blank, and a second chroma component mainly in another half of the blank, with the second chroma component not extending into the half with mainly the first chroma component. The green body is substantially opaque and white. The green body has a brightness/lightness $L^*$ value between 10 to 30 for a pre-sintered green body zirconia sample thickness of 1 to 1.3 mm in accordance with CIE $L^*a^*b^*$ colorimetric system, wherein, when measured for $L^*$ value of a CIE $L^*a^*b^*$ colorimetric system using the VITA Easyshade® Compact spectrophotometer, the $L^*$ value of the pre-sintered green body zirconia sample is read with the reading tip of the spectrophotometer to be set flush with, in close touching contact, and perpendicular to the measured surface of the pre-sintered green body zirconia sample.

In addition, the invention provides a dental block for producing a dental prosthesis, the dental block comprising a green body comprising 60-99.9 wt % zirconia that is soft sintered or pre-sintered. The green body has multiple different layers, each having a different chemical composition between adjacent layers, and being substantially opaque and white with a substantially consistent optical characteristic of color intensity/chroma across the layers. The different chemical composition includes different amounts of manganese or neodymium as a brightness/lightness $L^*$ value decreasing component between adjacent layers. The green body has a brightness/lightness $L^*$ value between 10 to 30 for a pre-sintered green body zirconia sample thickness of 1 to 1.3 mm in accordance with CIE $L^*a^*b^*$ colorimetric system, wherein, when measured for $L^*$ value of a CIE $L^*a^*b^*$ colorimetric system using the VITA Easyshade® Compact spectrophotometer, the $L^*$ value of the pre-sintered green body zirconia sample is read with the reading tip of the spectrophotometer to be set flush with, in close touching contact, and perpendicular to the measured surface of the pre-sintered green body zirconia sample. The green body is subsequently millable, and sinterable to form the dental prosthesis with the multiple different layers having different optical characteristics of gray color intensity towards a lower area of the prosthesis after sintering.

Furthermore, the invention provides a method for making a dental blank for use in producing a dental prosthesis, the method comprising:

a) forming zirconia and yttria into a desired shape while increasing an amount of manganese or neodymium as a brightness/lightness $L^*$ value decreasing component through a thickness of the desired shape towards a lower area; and b) pre-sintering or soft sintering the desired shape to form a green body dental blank with a different chemical composition of the amount of manganese or neodymium as a coloring agent through the thickness and being substantially opaque with a substantially consistent optical characteristic of color intensity/chroma across the thickness, the green body having a brightness/lightness $L^*$ value between 10 to 30 for a pre-sintered green body zirconia sample thickness of 1 to 1.3 mm in accordance with CIE $L^*a^*b^*$ colorimetric system wherein, when measured for $L^*$ value of a CIE $L^*a^*b^*$ colorimetric system using the VITA Easyshade® Compact spectrophotometer, the $L^*$ value of the pre-sintered green body zirconia sample is read with the reading tip of the spectrophotometer to be set flush with, in close touching contact, and perpendicular to the measured surface of the pre-sintered green body zirconia sample.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1a is a perspective view of a green body dental blank in accordance with an embodiment of the present invention;

FIG. 1b is a perspective view of another green body dental blank in accordance with another embodiment of the present invention;

FIG. 2a is a cross-sectional side schematic view of either of the green body dental blanks of FIGS. 1a and 1b, with layers thereof having different chemical compositions, such as different amounts of manganese;

FIG. 2b is table showing different areas with different amounts of manganese;

Figure 3:
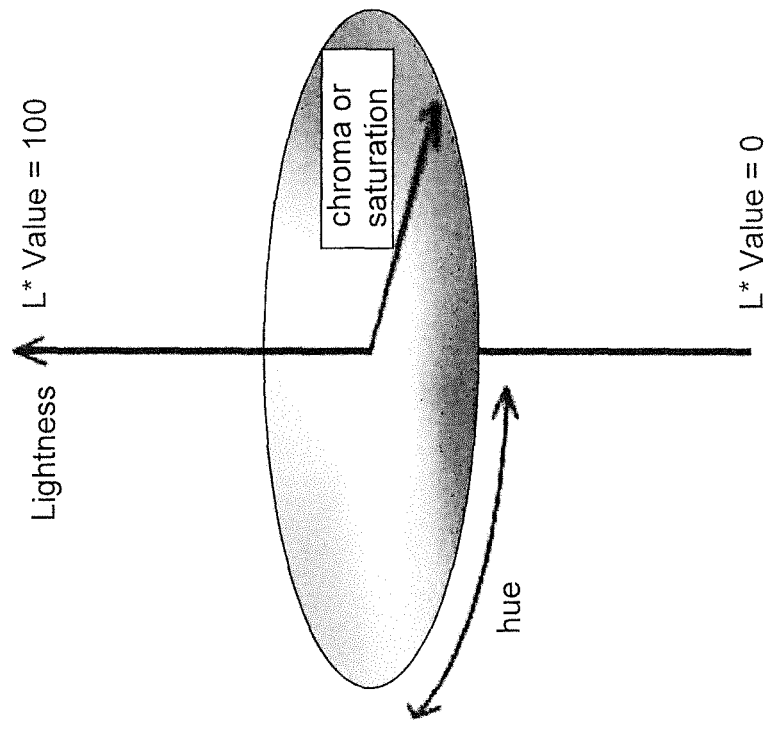
FIG. 3 is a schematic of the CIE L*a*b* colorimetric system to help understand the color aspect of the current invention.
Figure 3:
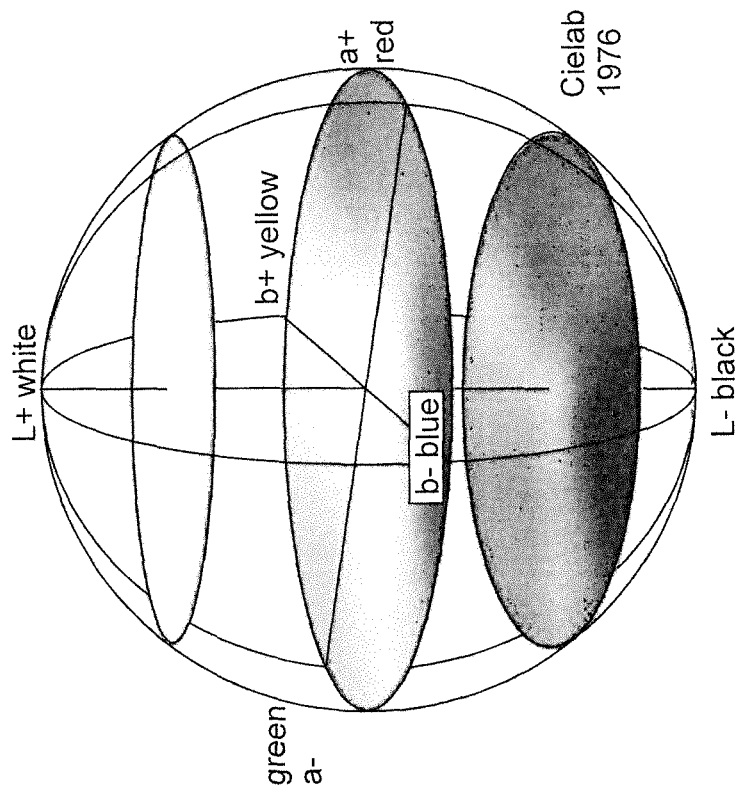

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The terms "zirconia green body" and "green body" are used interchangeably herein to mean a three-dimensional granular structure comprised of zirconia oxide particles, which is not sintered yet or, more frequently referred to, is partially sintered, pre-sintered or soft sintered at a temperature of 900-1100° C., to facilitate millability of the disc/blank. The terms "green body dental prosthesis" and "green dental prosthesis" are used interchangeably herein to mean a dental prosthesis that has been milled from the green body, but has not yet been sintered to become the final dental prosthesis.

The terms "pre-sintering" and "soft sintering" and "partial sintering" are used interchangeably herein to mean a reduction of size and/or number or the elimination of interparticle pores in a granular structure comprised of particles by heating, without melting, of the particles. Pre-sintering is carried out at a temperature of around 900-1100° C. to facilitate the machine milling of molded zirconia disc/blank. After pre-sintering zirconia is still porous and as a result becomes easy for color-ion liquid application. Pre-sintering or soft sintering is performed on the cast or molded zirconia to obtain a green body with sufficient strength to be milled.

The terms "sintering" and "primary sintering" and "final sintering" are used interchangeably herein. After the green body of the specific dental restoration (or green body dental prosthesis or green dental prosthesis) is ready from the milling, primary/final sintering is done at a much higher temperature (around 1300-1600° C.) than pre-sintering. After primary sintering, zirconia gets full densification, over 99%, and reaches its full flexural strength. Sintering is performed on the milled (and colored) green body dental prosthesis to obtain a dental prosthesis with final strength and optical characteristics, such as translucency and/or color intensity/chroma.

The term "zirconia" refers to various stoichiometries for zirconium oxides, most typically $ZrO_2$, and may also be known as zirconium oxide or zirconium dioxide. The zirconia may contain up to 20 weight percent of oxides of other chemical elements such as, for example, oxides of yttrium (e.g., $Y_2O_3$).

The term "ceramic" means an inorganic non-metallic material that is produced by application of heat. Ceramics are usually hard, porous and brittle and, in contrast to glasses or glass ceramics, display an essentially purely crystalline structure.

The term "glass ceramic" means an inorganic non-metallic material where one or more crystalline phases are surrounded by a glassy phase.

The term "dental milling disc/blank" is a solid form of various shapes, e.g., disc or block or any shape that can be fixedly attached to the dental milling machine. Diameter for disc shape is usually 100-90 mm, with various thickness of 10-25 mm for multiple-prostheses milling. Blocks may be about 20 mm to about 30 mm in two dimensions (width and height), for example, and may be of a certain length in a third dimension. The disc, blank or block can have a diameter greater than a thickness, and a longitudinal axis perpendicular to the thickness.

The term "thickness" when used in reference to the green body, green body dental prosthesis, or the dental prosthesis refers to a particular direction aligned in the thickness or height of the green body or dental prosthesis, and can be from a lower layer or portion of the green body or dental prosthesis (corresponding to an incisal area of a tooth) to an upper layer or portion of the green body or dental prosthesis (corresponding to a cervical area of a tooth), such as an increasing translucency or decreasing chroma from the lower layer or portion (incisal) to the upper layer or portion (cervical).

Description

The current invention relates to a method of fabricating yttria stabilized polycrystalline zirconia discs/blanks to produce dental prostheses using CAD/CAM processes. This inventive ceramic disc/blank does not have any optical gradation properties in the green stage before primary sintering. Dental prostheses made of this material take on similar optical properties found in natural human teeth only after the coloring and sintering stage.

Computer-aided design/computer-aided manufacturing (CAD/CAM) processes and equipment have been widely utilized in the dental industry. In these processes a three-dimensional image of a stump of a tooth (prepared tooth) is created along with the teeth surrounding the stump in an effort to create a dental restoration (dental prosthesis) which is to be placed over the stump. This image is displayed on a computer screen. Based on the stump (prepared tooth) and surrounding teeth, the dental technician may then select a tooth from a plurality of tooth library forms stored in the computer to best fit the stump. The selected tooth is projected onto the stump until an optimum positioning and fit of the dental restoration is achieved by dental design software. The digital data concerning the dental restoration thus formed are supplied to a numerically controlled milling machine operating in three dimensions. The milling machine cuts a blank of ceramic material, typically zirconia, into the dental restoration design based on the data supplied.

As illustrated in FIGS. 1a-2b, a zirconia green body with a generally round disc shape, indicated generally at 1 in FIG. 1a, or a zirconia green body with a generally rectangular block shape, indicated at 2 in FIG. 1b, in example implementations in accordance with the invention are shown. The restoration is nested as in FIG. 2a. The restoration(s) can be milled from the green bodies 1 and 2. In FIGS. 1a, 1b and 2a, an outline of potential restorations that can be milled from the blanks is shown superimposed on the blanks so that portions of the blank (e.g. layers, areas, portions or halves) corresponding to portions of the restoration (e.g. incisal and cervical) can be identified. The green body has multiple different layers, areas, portions or halves (A, B and C in FIGS. 1a and 1b, and areas 1, 2, 3, 4 and 5 in FIG. 2). Each of the different layers, areas, portions or halves has a different chemical composition between adjacent layers, areas, portions or halves. The green body 1 or 2 has first chroma components mainly in one (or a first) layer, area, portion or half of the blank (for example, areas A and B in FIG. 1a and FIG. 1b), and second chroma components mainly in another (or a second) layer, area, portion or half of the blank (for example area C in FIG. 1a and FIG. 1b). The second chroma components do not extend into the (first) layer, area, portion or half (for example areas A and B in FIG. 1a and FIG. 1b) with the first chroma components. Thus, the second chroma components are confined or limited to the another (or second) layer, area, portion or half of the blank (for example C in FIGS. 1a and 1c, or areas 1-4 in FIG. 2a). In FIG. 2a, the second chroma components exists from area 1 to area 4, and do not extend into the (first) layer, area, portion or half with the first chroma components (or that consists mainly of the first chroma components).

The first chroma components may include at least one of ferric, chrome, erbium or no color at all. These components may be added mainly in one (or the first) layer, area, portion or half of the blank (A and B in FIGS. 1a and 1b, area 5 in FIG. 2a) to make the shaded blank. When no chroma components are added, the blank can be a bleach shade. The first chroma components may further extend into the other (or the second) layer, area, portion or half of the blank (C in FIGS. 1a and 1b, areas 1-4 in FIG. 2a).

The second chroma components may include at least one of manganese oxide, manganese acetate, manganese chloride, neodymium oxide, copper, or cobalt. These components create a slightly gray, bluish, grayish blue, grayish violet effect thereby mimicking the natural appearance of a tooth. The second chroma components may be added mainly in the another (or the second) layer, area, portion or half of the blank (C in FIGS. 1a and 1b, areas 1-4 in FIG. 2a); but the second chroma components do not extend into the (first) layer, area, portion or half with the first chroma components (A and B in FIGS. 1a and 1b, area 5 in FIG. 2a).

In one aspect, a lowermost layer (C in FIGS. 1a and 1b, area 1 in FIG. 2a) can have the greatest amount of the second chroma component, such as manganese or neodymium, while the uppermost layer (A in FIGS. 1a and 1b, area 5 in FIG. 2a) can be without any of the second chroma component, and can be comprises solely of the first chroma component. Intermediate layers (B in FIGS. 1a and 1b, areas 2-4 in FIG. 2a) can have different but lesser amounts of the second chroma component. In one aspect, the layers can be distinct layers with distinct boundary layers characterized by distinct changes in the amount of the second chroma component or chemical composition. In another aspect, the layers can be areas or portions with gradual, rather than distinct, changes in chemical composition or the second chroma component. In one aspect, the layers, areas or portions with the second chroma component (C in FIGS. 1a and 1b, areas a-4 in FIG. 2a) can be small compared to the layer, area or portion without the second chroma component, such as less than half of a thickness of the blank. In another aspect, the layers, areas or portions can constitute halves, with the first chroma components mainly in the upper half of the blank, and the second chroma components mainly in the lower half of the blank, with the second chroma components not extending into the upper half of the blank than consists mainly of the first chroma components. Each of the halves can be an equal thickness of the whole blank with both halves constituting the entire thickness of the blank. In another aspect, the second chroma component can extend through a half of the thickness of the blank, while the remaining half has only the first chroma component.

For the increased translucent appearance, for example, zirconia powder is coated (or doped) with nano-sized manganese oxide (or manganese metal-ion) to produce a manganese oxide-coated zirconia powder (or manganese metal-ion doped zirconia powder). This powder is added incrementally towards the lower area, as in area 1 of FIG. 2a, of the dental zirconia blank.

Method of Making Manganese Slurry—Gray Color Source

One gram (1 g) of nano-sized manganese oxide was mixed with 1 kilogram (1 kg) of zirconia ($ZrO_2$). This makes a first mixture of manganese source that contains 0.1 wt percent (0.1 wt %) of manganese. This first mixture was sintered at a high temperature to create a second mixture of manganese-coated zirconia powder.

Or alternatively, zirconia was mixed with manganese metal-ion solution and the solution was evaporated and heat treated 800° C. to produce a second mixture of manganese-doped zirconia powder.

This second mixture was put in deionized water to make a primary manganese-zirconia slurry. The solid content of the primary slurry was at least higher than 50 wt % in the solution. Some other dispersant component was also added to increase the mixing characteristics.

The zirconia ($ZrO_2$) was used to prepare a white zirconia ($ZrO_2$) slurry. The solid content of the slurry was at least higher than 50 wt % in the solution.

1.5 gram of primary manganese-zirconia slurry was added to a 100 gram of white zirconia slurry. This makes a diluted secondary manganese-zirconia slurry (referred as M00196 hereafter). If all slurry were used 55 wt % by solid contents, as a result the total weight of manganese oxide in the primary manganese-zirconia slurry was 0.000825 gram. (1.5 gram×55 wt %×0.1 wt %). The total weight of zirconia ($ZrO_2$) in the primary manganese-zirconia slurry was 0.825 gram. (1.5 gram×55 wt %). So the manganese source in the secondary manganese-zirconia slurry was 0.001478 wt %. (manganese 0.000825 gram/(zirconia 55 gram+zirconia 0.825 gram)). This secondary manganese-zirconia slurry is a diluted form of primary manganese-zirconia slurry. This secondary manganese-zirconia slurry (M00196) is referred as manganese slurry hereafter.

Method of Creating Different Areas with Proportionally Different Amount of Manganese Component As shown in Table 1, the first test was done using manganese slurry along with white zirconia slurry. Slurry (suspension or colloidal liquid) for Area 1 to create the zirconia green body was prepared by mixing 50 wt % of manganese slurry (M00196) and 50 wt % of white zirconia slurry that does not have any color pigment in it. This first slurry was poured first on the casting mold to create the Area 1. Next, slurry (suspension or colloidal liquid) for Area 2 to create the zirconia green body was prepared by mixing 35 wt % of manganese slurry (M00196) and 65 wt % of white zirconia slurry that does not have any color pigment in it. Subsequently, Area 3, Area 4 and Area 5 were prepared in the proportion as shown in the table 1 and poured on the casting mold to create the entire zirconia green body.

Following table 1 shows the effect of manganese incrementally added on each area that do not contain any color component.

TABLE 1

| Area | Manganese slurry (M00196) (weight %) | Non-shaded zirconia slurry (weight %) | Manganese source weight % as opposed to zirconia powder | Level of grayness after final sintering | CIE L* Value after final sintering |
|---|---|---|---|---|---|
| Area 5 | 0% | 100% | 0 wt % | Least grayish | higher than area 4 (94.7) |
| Area 4 | 13% | 37% | less than area 3 | Less gray than area 3 | higher than area 3 (90.3) |
| Area 3 | 25% | 75% | less than area 2 | Less gray than area 2 | higher than area 2 (88.4) |
| Area 2 | 35% | 65% | less than area 1 | Less gray than area 1 | higher than area 1 (85.5) |
| Area 1 | 50% | 50% | 0.00148 wt % | Most grayish | Lowest (84.9) |

As seen in Table 1, the more manganese added the grayer the lower area becomes and the CIE L* value gets smaller or lower for the finally sintered parts. This green body or sintered body has been called 'white multi' zirconia since the green body or sintered body does not take on natural tooth color that is typically found on the body/cervical portion of the human tooth like ivory, yellow, brown or reddish brown. This green body can be milled using CAD/CAM method and subsequently dipped in color liquid, like VITA A2 shade or A3 shade for example. Then, after final sintering at around 1000° C. to 1500° C. the restoration takes a natural color with incisal graying effect like human tooth.

Alternatively, manganese metal-ion liquid can be penetrated into the lower area by vacuum suctioning method. Specifically, one end of the green body, the lower side for example, can be partially submerged into the manganese metal-ion liquid and vacuum can be applied so that only the lower area can be colored by manganese color source. In this case, there are not distinct layers to be seen and individual pouring for each area is not needed. Instead, one pour in slip casting is possible for multi-layer effects. One continuous light gray area is created from area 1 through area 5 without creating a distinct layer or boundary between layers.

Method of Making Ferric Slurry—Yellow Color Source

Six grams (6 g) of nano-sized ferric oxide was mixed with 1.5 kilogram (1.5 kg) of zirconia ($ZrO_2$). This makes a first mixture of ferric source that contains 0.1 wt percent (0.1 wt %) of ferric. This first mixture was sintered at high temperature to create a second mixture of ferric-coated zirconia powder.

Or alternatively, zirconia was mixed with ferric metal-ion solution and the solution was evaporated and heat treated at 800° C. to produce a second mixture of ferric-doped zirconia powder.

This second mixture was put in deionized water to make a primary ferric-zirconia slurry. The solid content of the primary slurry was at least higher than 50 wt % in the solution. Some other dispersant component was also added to increase the mixing characteristics.

The zirconia ($ZrO_2$) was used to prepare a white zirconia ($ZrO_2$) slurry. The solid content of the slurry was at least higher than 55 wt % in the solution.

1.5 gram of primary ferric-zirconia slurry was added to a 100 gram of zirconia slurry. This makes a secondary ferric-zirconia slurry (referred as F00196 hereafter). If all slurry were used 55 wt % by solid contents. As a result, the total weight of ferric oxide in the primary ferric-zirconia slurry was 0.000825 gram. (1.5 gram×55 wt %×0.1 wt %). The total weight of zirconia ($ZrO_2$) in the primary ferric-zirconia slurry was 0.825 gram. (1.5 gram×55 wt %). So the ferric source in the secondary ferric-zirconia slurry was 0.001478 wt %) (Ferric 0.000825 gram/(zirconia 55 gram+zirconia 0.825 gram)). This secondary ferric-zirconia slurry is a diluted form of primary ferric-zirconia slurry. This secondary ferric-zirconia slurry (F00196) is referred as ferric slurry hereafter.

Method of Making Chrome Slurry—Brown Color Source

Chrome slurry was made using the same method introduced above for making manganese slurry and ferric slurry. These two color slurries, i.e., secondary ferric-zirconia slurry and secondary chrome-zirconia slurry as a diluted form, were used as color shaded zirconia slurry. Here in table 2, specific weight of secondary ferric-zirconia slurry and specific weight of secondary chrome-zirconia slurry were used to make VITA A2 shade.

As shown in Table 2, the second test was done using ferric slurry and chrome slurry along with manganese slurry. Slurry (suspension or colloidal liquid) for Area 1 to create the zirconia green body was prepared by mixing 50 wt % of manganese slurry (M00196) mentioned above and 50 wt % of primary ferric-zirconia slurry and primary chrome-zirconia slurry for shade effect. This first slurry was poured first on the casting mold to create the Area 1. Next, slurry (suspension or colloidal liquid) for Area 2 to create the zirconia green body was prepared by mixing 35 wt % of manganese slurry (M00196) and 65 wt % of primary ferric-zirconia slurry and primary chrome-zirconia slurry for shade effect. Subsequently, Area 3, Area 4 and Area 5 were prepared in the proportion as shown in the table 1 and poured on the casting mold to create the entire zirconia green body.

Following Table 2 shows the effect of manganese incrementally added on each area that has color components.

TABLE 2

| Area | Manganese slurry (M00196) (weight %) | Color (A2)-shaded zirconia slurry (weight %) | Manganese source weight % vs zirconia powder | Level of grayness after final sintering | CIE Value after final sintering | | |
|---|---|---|---|---|---|---|---|
| | | | | | L | a | b C |
| Area 5 | 0% | 100% | 0 wt % | Least grayish | higher than area 4 (83.3) | 2.3 | 37.4 37.5 |
| Area 4 | 13% | 87% | less than area 3 | Less gray than area 3 | higher than area 3 (81.2) | 1.3 | 31.5 31.5 |
| Area 3 | 25% | 75% | less than area 2 | Less gray than area 2 | higher than area 2 (80.1) | 1.3 | 28.0 28.0 |

TABLE 2-continued

| Area | Manganese slurry (M00196) (weight %) | Color (A2)-shaded zirconia slurry (weight %) | Manganese source weight % vs zirconia powder | Level of grayness after final sintering | CIE Value after final sintering L | a | b | C |
|---|---|---|---|---|---|---|---|---|
| Area 2 | 35% | 65% | less than area 1 | Less gray than area 1 | higher than area 1 (79.2) | 0.9 | 23.1 | 23.2 |
| Area 1 | 50% | 50% | 0.00148 wt % | Most grayish | Lowest (74.9) | 2.5 | 20.9 | 21.1 |

As the amount of manganese is increased and color component is decreased towards the lower area, as in from layer 5 towards layer 1, the level of gray color is increased and chroma intensity (C) is decreased. This is the same characteristics found in actual human tooth.

Alternatively, manganese metal-ion liquid can be penetrated into the lower area by vacuum suctioning method. Specifically, one end of the green body, the lower side for example, can be partially submerged into the manganese metal-ion liquid and vacuum can be applied so that only the lower area can be colored by manganese color source. In this case, there are not distinct layers to be seen and individual pouring for each area is not needed. Instead, one pour in slip casting is possible for multi-layer effects. One continuous light gray area is created from area 1 through area 5 without creating a distinct layer or boundary between layers.

In the pre-sintering stage, the inventors found that the amount of open pores between grains are important because it determines the efficiency level of coloring at the later stage. The more open pores, the weaker the green body, but higher coloring efficiency; and the less the amount of open pores, the stronger the green body but lower coloring efficiency. The level of open pores that contain air can determine the desired green body strength for milliability and the efficiency of green body coloring. The level of amount of open pores can be expressed, for example, by L* value from the CIEL*a*b* colorimetric system.

The L*a*b* colorimetric system in FIG. 3 was standardized in 1976 by Commission Internationale de l'Eclairage (CIE). In the system, a lightness/brightness is defined as L* and expressed by a numerical value of from O to 100, in which L*=O means that the color is complete black, and L*=100 means that the color is complete white.

When advanced ceramics with poly-crystal structures contain substantially no residual pores after being fully sintered, the L* value goes up to as high as 60-85 for the samples with thickness of 1 mm, thereby characterized with good light transmission. When the zirconia green body is partly sintered, i.e. in a pre-sintered stage, it contains open pores/air which causes the diffusion of light, resulting in a much lower L* value number.

The inventors discovered that the higher this L* value number for the zirconia green body, the harder it is to mill and more difficult it is to be penetrated with color-ion liquids. The lower the number, the weaker the green body, causing cracks and chipping during the milling process and making it more difficult to control the coloring consistency at later stage. It was found that the ideal L* value, when expressed in CIE L*a*b* colorimetric system in a standard illuminant D65, is between 10 and 30 in one aspect, 10 and 20 in another aspect, and 15 and 20 in another aspect; when measured for L* value of a CIE L*a*b* colorimetric system using the VITA Easy Shade® Compact spectrophotometer, the L* value of the pre-sintered green body zirconia sample 29 is read with the reading tip of the spectrophotometer to be set flush with, in close touching contact, and perpendicular to the measured surface of the pre-sintered green body zirconia sample.

Figure 4A:
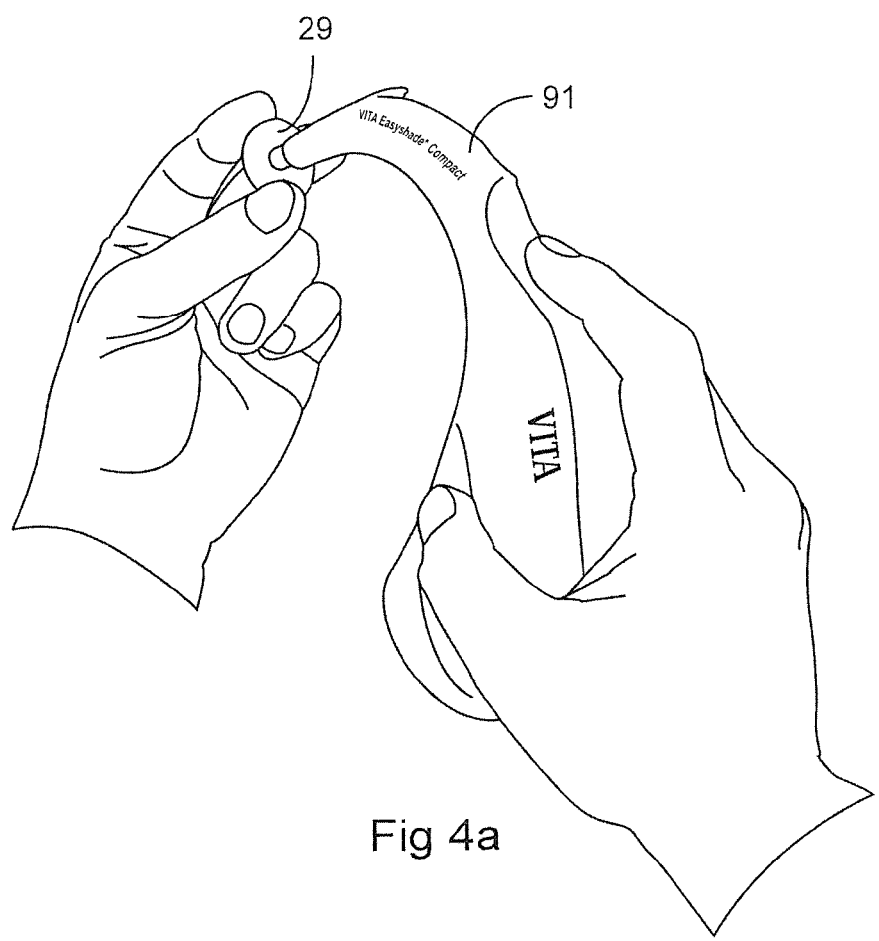
FIGS. 4a and 4b are schematic views of a color chroma measuring method using a hand-held spectrophotometer.
Figure 4B:
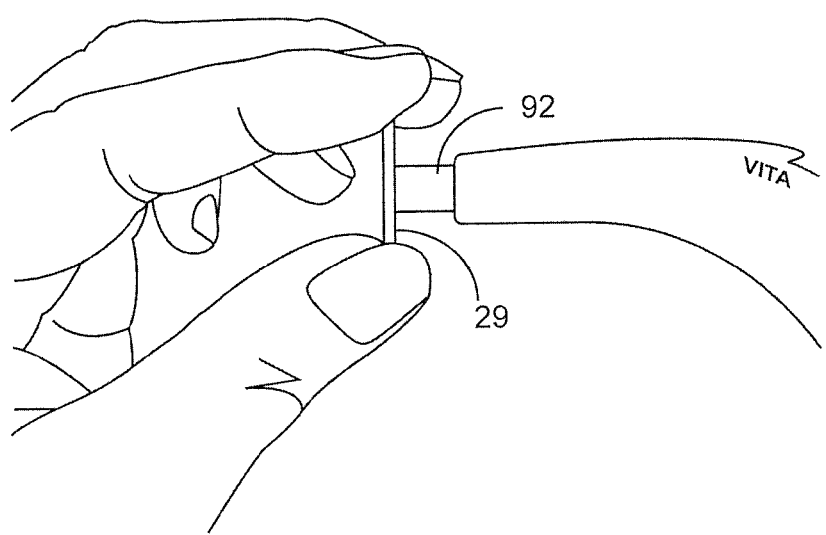

Specifically, when measured for L* value of a CIEL*a*b* colorimetric system using the VITA Easyshade® Compact spectrophotometer (VITA, Germany, www.vita-zahnfabrik.com) 91 as in FIG. 4a, which is most widely used for color analysis in dental office/laboratory, the L* value of the current invention, from a pre-sintered green body zirconia sample 29 with a diameter of 15 mm and thickness of 1.00 to 1.30 mm, is 10-30 in one aspect, 10-20 in another aspect or 15-20 in another aspect from single and/or multi-mode. The samples were measured according to the user manual in such a way as for the reading tip 92 of the spectrophotometer 91 to be set flush with, in close touching contact, and perpendicular to the measured surface of the pre-sintered green body zirconia sample 29, as shown in FIG. 4b. Since the VITA Easyshade® has a built-in light source inside the tip area, the ideal L* value of 10-30, or 10-20, or 15-20 were independent of the amount of light in a normal office room setting.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A dental block device for producing a dental prosthesis, the dental block device comprising:
   a) a green body comprising zirconia;
   b) the green body having multiple different layers each having a different chemical composition between adjacent layers;
   c) the green body having a first chroma component mainly in one half of the blank, and a second chroma component mainly in another half of the blank, with the second chroma component not extending into the half with mainly the first chroma component;
   d) the green body being substantially opaque and white; and
   e) the green body having a brightness/lightness L* value between 10 to 30 for a pre-sintered green body zirconia sample thickness of 1 to 1.3 mm in accordance with CIE L*a*b* colorimetric system wherein, when measured for L* value of a CIE L*a*b* colorimetric system using the VITA Easyshade® Compact spectrophotometer, the L* value of the pre-sintered green body zirconia sample is read with the reading tip of the spectrophotometer to be set flush with, in close touching contact, and perpendicular to the measured surface of the pre-sintered green body zirconia sample.

2. The device in accordance with claim 1, wherein the green body is a colored blank.

3. The device in accordance with claim 1, wherein the green body is an uncolored blank.

4. The device in accordance with claim 1, wherein the first chroma component includes at least one of ferric, chrome, or erbium.

5. The device in accordance with claim 1, wherein the second chroma component includes at least one of manganese oxide, manganese acetate, manganese chloride, neodymium oxide, copper, or cobalt.

6. The device in accordance with claim 1, wherein the multiple different layers have different thicknesses with respect to one another with a lower layer having a thickness between 0.1-5 mm and an upper layer having a thickness between 0.1-5 mm.

7. The device in accordance with claim 1, further comprising:
the green body is subsequently millable and sinterable to form the dental prosthesis with the multiple different layers having different optical characteristics of gray color intensity towards a upper area of the prosthesis after sintering.

8. The device in accordance with claim 1, wherein the green body has a brightness/lightness $L^*$ value between 10 to 20 for a sample thickness of 1 to 1.3 mm in accordance with CIE $L^*a^*b^*$ colorimetric system.

9. A dental block device for producing a dental prosthesis, the dental block device comprising:
 a) a green body comprising 60-99.9 wt % zirconia that is soft sintered or pre-sintered;
 b) the green body having multiple different layers each having a different chemical composition between adjacent layers and being substantially opaque and white with a substantially consistent optical characteristic of color intensity/chroma across the layers;
 c) the different chemical composition including different amounts of manganese or neodymium as a brightness/lightness $L^*$ value decreasing component between adjacent layers;
 d) the green body having a brightness/lightness $L^*$ value between 10 to 30 for a pre-sintered green body zirconia sample thickness of 1 to 1.3 mm in accordance with CIE $L^*a^*b^*$ colorimetric system wherein, when measured for $L^*$ value of a CIE $L^*a^*b^*$ colorimetric system using the VITA Easyshade® Compact spectrophotometer, the $L^*$ value of the pre-sintered green body zirconia sample is read with the reading tip of the spectrophotometer to be set flush with, in close touching contact, and perpendicular to the measured surface of the pre-sintered green body zirconia sample; and
 e) the green body is subsequently millable, and sinterable to form the dental prosthesis with the multiple different layers having different optical characteristics of gray color intensity towards a lower area of the prosthesis after sintering.

10. The device in accordance with claim 9, wherein the green body is millable to form a green dental prosthesis that is colorable and sinterable to form the dental prosthesis with the multiple different layers having different optical characteristics of gray color intensity towards the upper area of the prosthesis after sintering.

11. The device in accordance with claim 10, wherein the multiple different layers have different thicknesses with respect to one another with the lower layer having a thickness between 0.1-5 mm and an upper layer having a thickness between 0.1-5 mm.

12. The device in accordance with claim 9, further comprising:
the green body having a first chroma component mainly in one half of the blank, and a second chroma components mainly in another half of the blank, with the second chroma component not extending into the half with mainly the first chroma component.

13. The device in accordance with claim 9, wherein the green body has a brightness/lightness $L^*$ value between 10 to 20 for a sample thickness of 1 to 1.3 mm in accordance with CIE $L^*a^*b^*$ colorimetric system.

* * * * *

UNITED STATES PATENT AND TRADEMARK OFFICE
CERTIFICATE OF CORRECTION

Page 1 of 1

PATENT NO. : 9,668,837 B2
APPLICATION NO. : 15/099914
DATED : June 6, 2017
INVENTOR(S) : Benjamin Y. Jung It is certified that error appears in the above-identified patent and that said Letters Patent is hereby corrected as shown below:

Column 12, Claim 9, Line 12, "lower" should be --upper--

Signed and Sealed this
Ninth Day of January, 2018

Joseph Matal
*Performing the Functions and Duties of the*
*Under Secretary of Commerce for Intellectual Property and*
*Director of the United States Patent and Trademark Office*